US009743974B2

(12) United States Patent
Gurskis et al.

(10) Patent No.: US 9,743,974 B2
(45) Date of Patent: Aug. 29, 2017

(54) POSITIONING METHOD AND APPARATUS FOR DELIVERING VAPOR TO THE UTERUS

(75) Inventors: Donnell William Gurskis, Belmont, CA (US); Robert Bilgor Peliks, Redwood City, CA (US); Hugh Edward Magen, San Francisco, CA (US); Roxanne Daniels, San Francisco, CA (US); Steven Robert Bacich, Half Moon Bay, CA (US)

(73) Assignee: AEGEA MEDICAL INC., Redwood City, CA (US)

( * ) Notice: Subject to any disclaimer, the term of this patent is extended or adjusted under 35 U.S.C. 154(b) by 1472 days.

(21) Appl. No.: 13/292,889

(22) Filed: Nov. 9, 2011

(65) Prior Publication Data
US 2012/0184949 A1 Jul. 19, 2012

Related U.S. Application Data

(60) Provisional application No. 61/411,840, filed on Nov. 9, 2010, provisional application No. 61/544,885, filed on Oct. 7, 2011.

(51) Int. Cl.
*A61B 18/04* (2006.01)
*A61B 18/00* (2006.01)

(52) U.S. Cl.
CPC ...... *A61B 18/04* (2013.01); *A61B 2018/0022* (2013.01); *A61B 2018/00559* (2013.01); *A61B 2018/00577* (2013.01)

(58) Field of Classification Search
CPC .. A61B 2018/00577; A61B 2018/0022; A61B 18/04; A61B 2018/00559
(Continued)

(56) References Cited

U.S. PATENT DOCUMENTS

| 408,899 A | 8/1889 | Small |
|---|---|---|
| 1,719,750 A | 7/1929 | Bridge et al. |

(Continued)

FOREIGN PATENT DOCUMENTS

| CN | 201189204 Y | 2/2009 |
|---|---|---|
| CN | 201379631 Y | 1/2010 |

(Continued)

OTHER PUBLICATIONS

Peliks et al.; U.S. Appl. No. 13/648,132 entitled "Integrity Testing Method and Apparatus for Delivering Vapor to the Uterus," filed Oct. 9, 2012.

(Continued)

*Primary Examiner* — Carl H Layno
*Assistant Examiner* — Erin M Piateski
(74) *Attorney, Agent, or Firm* — Shay Glenn LLP

(57) ABSTRACT

A method and system of providing therapy to a patient's uterus. The method can include the steps of inserting a uterine ablation device into the uterus; expanding a distal anchor; inflating a proximal balloon to pull the distal anchor proximally and seat the distal anchor against the internal os of the uterus; inflating a central balloon to seal the cervix; delivering vapor from the uterine ablation device into the uterus; and condensing the vapor on tissue within the uterus. The can include a cervical collar adapted to place a distal portion of the device within the uterus when the cervical collar contacts an external os of the cervix.

9 Claims, 15 Drawing Sheets

(58) Field of Classification Search
USPC .................................................. 606/27, 28
See application file for complete search history.

(56) References Cited

U.S. PATENT DOCUMENTS

| | | | |
|---|---|---|---|
| 3,871,374 A | 3/1975 | Bolduc et al. |
| 3,924,628 A | 12/1975 | Droegemueller et al. |
| 4,976,711 A | 12/1990 | Parins et al. |
| 5,045,056 A | 9/1991 | Behl |
| 5,084,044 A | 1/1992 | Quint |
| 5,122,138 A | 6/1992 | Manwaring |
| 5,242,474 A | 9/1993 | Herbst et al. |
| 5,277,201 A | 1/1994 | Stern |
| 5,437,629 A | 8/1995 | Goldrath |
| 5,443,470 A | 8/1995 | Stern et al. |
| 5,449,380 A | 9/1995 | Chin |
| 5,451,208 A | 9/1995 | Goldrath |
| 5,540,658 A | 7/1996 | Evans et al. |
| 5,542,928 A | 8/1996 | Evans et al. |
| 5,562,720 A | 10/1996 | Stern et al. |
| 5,665,074 A | 9/1997 | Kelly |
| 5,674,191 A | 10/1997 | Edwards et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,730,719 A | 3/1998 | Edwards |
| 5,743,870 A | 4/1998 | Edwards |
| 5,769,880 A | 6/1998 | Truckai et al. |
| 5,800,379 A | 9/1998 | Edwards |
| 5,810,764 A | 9/1998 | Eggers et al. |
| 5,820,580 A | 10/1998 | Edwards et al. |
| 5,836,906 A | 11/1998 | Edwards |
| 5,843,019 A | 12/1998 | Eggers et al. |
| 5,871,469 A | 2/1999 | Eggers et al. |
| 5,873,855 A | 2/1999 | Eggers et al. |
| 5,888,198 A | 3/1999 | Eggers et al. |
| 5,891,095 A | 4/1999 | Eggers et al. |
| 5,891,457 A | 4/1999 | Neuwirth |
| 5,902,272 A | 5/1999 | Eggers et al. |
| 6,004,509 A | 12/1999 | Dey et al. |
| 6,015,406 A | 1/2000 | Goble et al. |
| 6,024,733 A | 2/2000 | Eggers et al. |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,063,079 A | 5/2000 | Hovda et al. |
| 6,066,134 A | 5/2000 | Eggers et al. |
| 6,086,585 A | 7/2000 | Hovda et al. |
| 6,102,046 A | 8/2000 | Weinstein et al. |
| 6,105,581 A | 8/2000 | Eggers et al. |
| 6,109,268 A | 8/2000 | Thapliyal et al. |
| 6,113,597 A | 9/2000 | Eggers et al. |
| 6,117,109 A | 9/2000 | Eggers et al. |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,210,404 B1 | 4/2001 | Shadduck |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,277,114 B1 | 8/2001 | Bullivant et al. |
| 6,283,961 B1 | 9/2001 | Underwood et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,322,549 B1 | 11/2001 | Eggers et al. |
| 6,355,032 B1 | 3/2002 | Hovda et al. |
| 6,363,937 B1 | 4/2002 | Hovda et al. |
| 6,364,877 B1 | 4/2002 | Goble et al. |
| 6,379,351 B1 | 4/2002 | Thapliyal et al. |
| 6,391,025 B1 | 5/2002 | Weinstein et al. |
| 6,398,759 B1 | 6/2002 | Sussman et al. |
| 6,409,699 B1 | 6/2002 | Ash |
| 6,416,507 B1 | 7/2002 | Eggers et al. |
| 6,416,508 B1 | 7/2002 | Eggers et al. |
| 6,416,509 B1 | 7/2002 | Goble et al. |
| 6,432,103 B1 | 8/2002 | Ellsberry et al. |
| 6,440,089 B1 | 8/2002 | Shine |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,482,201 B1 | 11/2002 | Olsen et al. |
| 6,508,816 B2 | 1/2003 | Shadduck |
| 6,510,854 B2 | 1/2003 | Goble |
| 6,540,741 B1 | 4/2003 | Underwood et al. |
| 6,544,261 B2 | 4/2003 | Ellsberry et al. |
| 6,547,784 B1 | 4/2003 | Thompson et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,589,201 B1 | 7/2003 | Sussman et al. |
| 6,589,237 B2 | 7/2003 | Woloszko et al. |
| 6,595,990 B1 | 7/2003 | Weinstein et al. |
| 6,602,248 B1 | 8/2003 | Sharps et al. |
| 6,620,155 B2 | 9/2003 | Underwood et al. |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,669,694 B2 | 12/2003 | Shadduck |
| 6,676,628 B2 | 1/2004 | Sussman et al. |
| 6,708,056 B2 | 3/2004 | Duchon et al. |
| 6,712,811 B2 | 3/2004 | Underwood et al. |
| 6,719,754 B2 | 4/2004 | Underwood et al. |
| 6,726,684 B1 | 4/2004 | Woloszko et al. |
| 6,746,447 B2 | 6/2004 | Davison et al. |
| 6,749,604 B1 | 6/2004 | Eggers et al. |
| 6,763,836 B2 | 7/2004 | Tasto et al. |
| 6,766,202 B2 | 7/2004 | Underwood et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,780,180 B1 | 8/2004 | Goble et al. |
| 6,805,130 B2 | 10/2004 | Tasto et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,896,672 B1 | 5/2005 | Eggers et al. |

(56) References Cited

U.S. PATENT DOCUMENTS

| | | |
|---|---|---|
| 6,896,674 B1 | 5/2005 | Woloszko et al. |
| 6,911,028 B2 | 6/2005 | Shadduck |
| 6,915,806 B2 | 7/2005 | Pacek et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,960,204 B2 | 11/2005 | Eggers et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,094,215 B2 | 8/2006 | Davison et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,131,969 B1 | 11/2006 | Hovda et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,320,325 B2 | 1/2008 | Duchon et al. |
| 8,579,892 B2 | 11/2013 | Hoey et al. |
| 8,900,223 B2 | 12/2014 | Shadduck |
| 2002/0013601 A1 | 1/2002 | Nobles et al. |
| 2002/0019627 A1 | 2/2002 | Maguire et al. |
| 2002/0177846 A1 | 11/2002 | Mulier et al. |
| 2003/0217962 A1 | 11/2003 | Childers et al. |
| 2003/0220604 A1 | 11/2003 | Al-Anazi |
| 2004/0002698 A1 | 1/2004 | Hua Xiao et al. |
| 2004/0068306 A1 | 4/2004 | Shadduck |
| 2004/0199226 A1 | 10/2004 | Shadduck |
| 2005/0143728 A1 | 6/2005 | Sampson et al. |
| 2005/0171574 A1 | 8/2005 | Rubinsky et al. |
| 2005/0177147 A1 | 8/2005 | Vancelette et al. |
| 2006/0058831 A1* | 3/2006 | Atad .................. 606/193 |
| 2006/0135955 A1 | 6/2006 | Shadduck |
| 2006/0161233 A1 | 7/2006 | Barry et al. |
| 2006/0224154 A1 | 10/2006 | Shadduck et al. |
| 2006/0265053 A1 | 11/2006 | Hunt |
| 2007/0032814 A1* | 2/2007 | Hibler .................. 606/193 |
| 2007/0225744 A1 | 9/2007 | Nobles et al. |
| 2007/0239197 A1 | 10/2007 | Dubey et al. |
| 2007/0288051 A1* | 12/2007 | Beyer et al. .................. 606/193 |
| 2008/0132826 A1 | 6/2008 | Shadduck et al. |
| 2008/0135053 A1 | 6/2008 | Gruber et al. |
| 2008/0167664 A1 | 7/2008 | Payne et al. |
| 2008/0249467 A1 | 10/2008 | Burnett et al. |
| 2009/0024108 A1 | 1/2009 | Lee-Sepsick et al. |
| 2009/0054868 A1 | 2/2009 | Sharkey et al. |
| 2009/0054869 A1 | 2/2009 | Sharkey et al. |
| 2009/0054870 A1 | 2/2009 | Sharkey et al. |
| 2009/0054871 A1* | 2/2009 | Sharkey et al. ............. 604/515 |
| 2009/0125010 A1 | 5/2009 | Sharkey et al. |
| 2009/0216220 A1 | 8/2009 | Hoey et al. |
| 2009/0306640 A1 | 12/2009 | Glaze et al. |
| 2010/0078046 A1 | 4/2010 | Labib et al. |
| 2010/0082021 A1 | 4/2010 | Gutierrez et al. |
| 2010/0094270 A1 | 4/2010 | Sharma |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114089 A1 | 5/2010 | Truckai et al. |
| 2010/0262133 A1 | 10/2010 | Hoey et al. |
| 2011/0077628 A1 | 3/2011 | Hoey et al. |
| 2011/0112432 A1 | 5/2011 | Toth |
| 2011/0112433 A1 | 5/2011 | Toth |
| 2011/0112523 A1 | 5/2011 | Toth et al. |
| 2011/0118718 A1 | 5/2011 | Toth et al. |
| 2011/0118719 A1 | 5/2011 | Vissy et al. |
| 2011/0160648 A1 | 6/2011 | Hoey |
| 2011/0208178 A1 | 8/2011 | Truckai |
| 2012/0136343 A1 | 5/2012 | Burnett |
| 2012/0197245 A1 | 8/2012 | Burnett et al. |
| 2012/0209281 A1 | 8/2012 | Truckai |
| 2012/0232545 A1 | 9/2012 | Truckai et al. |
| 2012/0283717 A1 | 11/2012 | Sharkey et al. |
| 2013/0006231 A1 | 1/2013 | Sharma et al. |
| 2013/0296837 A1 | 11/2013 | Burnett et al. |

FOREIGN PATENT DOCUMENTS

| | | |
|---|---|---|
| EP | 2198797 A1 | 6/2012 |
| JP | H06-285074 A | 10/1994 |
| JP | 2000502585 A | 3/2000 |
| JP | 20003513742 A | 4/2003 |
| JP | 2010516351 A | 5/2010 |
| WO | WO 99/53853 A1 | 10/1999 |
| WO | WO 00/29055 A1 | 5/2000 |
| WO | WO 02/069821 A1 | 9/2002 |
| WO | WO 03/070302 A1 | 8/2003 |
| WO | WO 2006/055695 A1 | 5/2006 |
| WO | WO 2006108974 A1 | 10/2006 |
| WO | WO 2010/045055 A2 | 4/2010 |
| WO | WO 2010/048007 A1 | 4/2010 |
| WO | WO 2011/025658 A1 | 3/2011 |
| WO | WO 2011/053599 A1 | 5/2011 |
| WO | WO 2011/060189 A1 | 5/2011 |
| WO | WO 2011/060191 A1 | 5/2011 |
| WO | WO 2012/106260 A2 | 8/2012 |

OTHER PUBLICATIONS

Van De Velde; Vapo-cauterization of the uterus; Amer. J. Med. Sci.; vol. CXVIII (118); Nov. 1899.

Blacker; Vaporization of the uterus; J. Obstet. & Gyn.; pp. 488-511; May 1901.

Neuwirth et al.; The endometrial ablator: a new instrument; Obst. & Gyn.; vol. 83; No. 5; part 1; pp. 792-796; May 1994.

Prior et al.; Treatment of mennorrhagia by radiofrequency heating; Int. J. Hyperthermia; vol. 7; No. 2; pp. 213-220; Mar.-Apr. 1991.

Baker et al.; Threshold intrauterine perfusion pressures for intraperitoneal spill during hydrotubation and correlation with tubal adhesive diseases; Fertility and Sterility; 64(6); pp. 1066-1069; Dec. 31, 1995.

* cited by examiner

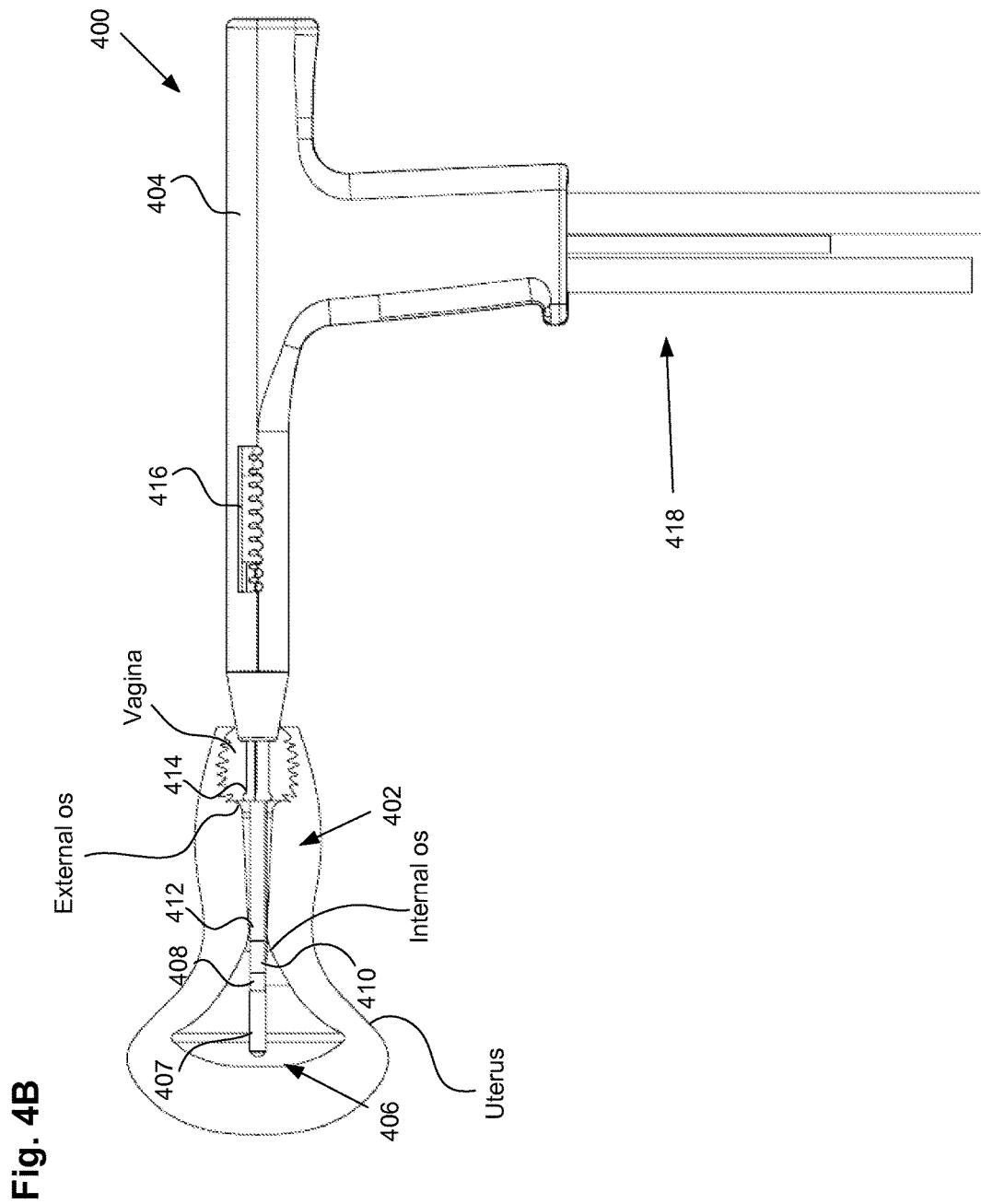

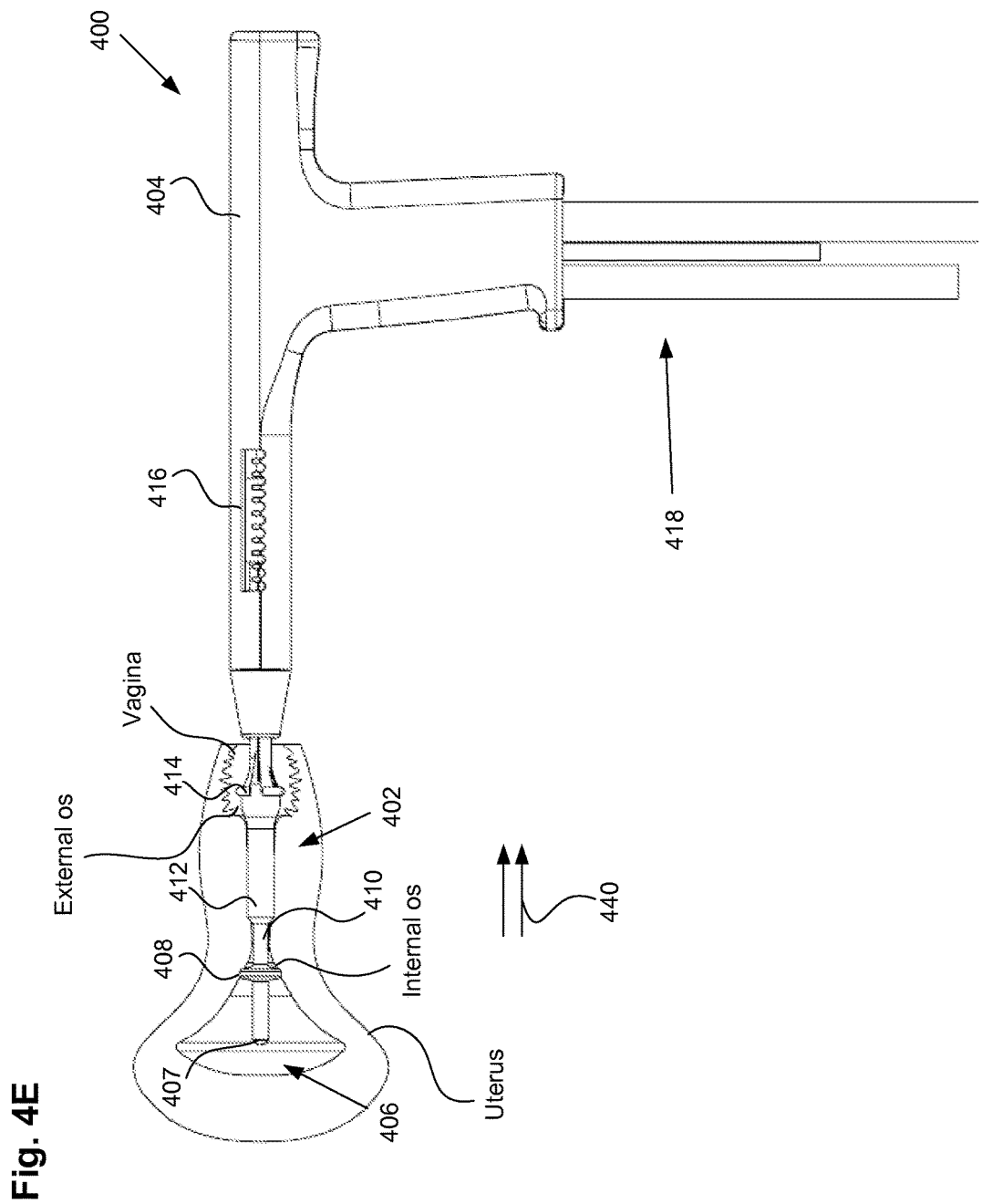

US 9,743,974 B2

POSITIONING METHOD AND APPARATUS FOR DELIVERING VAPOR TO THE UTERUS

CROSS REFERENCE TO RELATED APPLICATIONS

This application claims the benefit under 35 U.S.C. 119 of U.S. Provisional Patent Application No. 61/411,840, filed Nov. 9, 2010, titled "Uterine Vapor Therapy Device", and U.S. Provisional Patent Application No. 61/544,885, filed Oct. 7, 2011, titled "Positioning Method And Apparatus For Delivering Vapor to the Uterus".

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention generally relates to endometrial ablation. More specifically, the present invention relates to endometrial ablation with a heated vapor.

BACKGROUND OF THE INVENTION

Endometrial ablation (i.e., the removal or destruction of the endometrial lining of the uterus) is used as an alternative to hysterectomy for treating menorrhagia, or other uterine diseases. One prior technique for performing endometrial ablation employs a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting.

Some approaches make use of heated fluid to ablate the endometrium. For example, early journal articles describe the use of steam to treat uterine hemorrhage. See, e.g., Van de Velde, "Vapo-Cauterization of the Uterus," Amer. J. Med. Sci., vol. CXVIII (1899); Blacker, "Vaporization of the Uterus," J. Obstet. & Gyn., pp. 488-511 (c. 1901). The use of steam for this purpose was later discredited, apparently due to patient morbidity and mortality. See, e.g., Fuller U.S. Pat. No. 6,139,571. More recent descriptions of the use of injecting hot fluid into the uterus have been described. Uterine therapies employing a contained fluid have also been described.

One previous solution utilizes a balloon-based system using ultrasound as the energy source. High frequency, or radiofrequency (RF), energy has been used to perform thermal ablation of endometrial tissue. Current products for performing endometrial ablation include the NovaSure® procedure and a system marketed under the trade name THERMACHOICE®, by Ethicon, Inc. of Somerville, N.J. Cryogenic ablation, or "cryoablation," is another endometrial treatment approach.

SUMMARY OF THE DISCLOSURE

A method of delivering vapor to a uterus of a patient, comprising: inserting a portion of a uterine ablation device into the uterus of the patient; expanding a distal anchor of the uterine ablation device in the uterus; inflating a proximal balloon of the uterine ablation device to pull the uterine ablation device proximally and place the distal anchor against an internal os of the patient; inflating a central balloon within the cervical canal; and delivering a heated vapor to the uterus to ablate uterine tissue.

In some embodiments, the inserting step further comprises inserting the uterine ablation device into the uterus of the patient so as to position a distal tip of the device distally to the internal os of the patient.

In some embodiments, the expanding the distal anchor step further comprises inflating the distal anchor distally to the internal os of the patient.

In one embodiment, the distal anchor comprises a distal balloon. The distal balloon can comprise a donut shape.

In another embodiment, the distal anchor comprises a distal expandable frame.

In some embodiments, the inflating the proximal balloon step further comprises inflating the proximal balloon against a cervical canal, an external os, and a vagina of the patient.

In one embodiment, the inflating the central balloon step further comprises inflating the central balloon against a cervical canal and the internal os of the patient.

In some embodiments, the inflating the proximal balloon step is performed after the inflating the distal expansion mechanism step. In other embodiments, the central balloon step is performed after the inflating the proximal balloon step.

In one embodiment, the method comprises, prior to the delivering step, collapsing the distal anchor of the uterine ablation device.

A uterine ablation device is also provided, comprising a shaft sized and configured to access a uterus of a patient, the shaft being coupled to a vapor source, vapor delivery ports disposed on a distal portion of the shaft, a distal anchor positioned proximally on the shaft from the vapor delivery ports, a central balloon positioned proximally to the distal anchor, the central balloon configured to contact an internal os and a cervical canal of the patient when the distal anchor is positioned in the uterus against the internal os, and a proximal balloon positioned proximally to the sealing balloon, the proximal balloon configured to span from the cervical canal into a vagina of the patient when the distal anchor is positioned against the internal os.

In some embodiments, the device further comprises a filter portion disposed on the distal portion of the shaft, the filter portion configured to remove vapor from the uterus but prevent removal of tissue, blood clots, or debris from the uterus.

In some embodiments, the central balloon has a length along the shaft of approximately 15 mm to 25 mm.

In another embodiment, the distal anchor has a length along the shaft of approximately 3 mm to 10 mm.

In some embodiments, the proximal balloon has a length along the shaft of approximately 50 mm to 70 mm.

A method of delivering vapor to a uterus of a patient with a uterine ablation device is also provided, comprising inserting a distal tip of the uterine ablation device inside the uterus, positioning a distal anchor of the uterine ablation device within the uterus distally from an internal os, positioning a proximal balloon of the uterine ablation device partially within a cervical canal and partially within a vagina of the patient, positioning a central balloon of the uterine ablation device within the cervical canal, expanding the distal anchor, after expanding the distal anchor, inflating the proximal balloon to pull the distal anchor proximally against the internal os, after inflating the proximal balloon, inflating the central balloon to seal the cervical canal, and delivering a heated vapor to the uterus to ablate uterine tissue.

A uterine ablation device is provided comprising a shaft sized and configured to access a uterus of a patient, the shaft comprising a vapor delivery lumen and a vapor removal lumen, vapor delivery ports disposed on a distal portion of the shaft and coupled to the vapor delivery lumen, at least one vapor removal port disposed on the distal portion of the shaft and coupled to the vapor removal lumen, a filter disposed over the at least one vapor removal port, a distal anchor positioned proximally on the shaft from the vapor delivery ports; a central balloon positioned proximally from the distal anchor, the central balloon having a length along the shaft of approximately 15 mm to 25 mm, and a proximal balloon positioned proximally from the central balloon, the proximal balloon configured having a length along the shaft of approximately 50 mm to 70 mm.

In some embodiments, the vapor delivery lumen is disposed within the vapor removal lumen.

In another embodiment, the vapor delivery ports, the at least one vapor removal port, and the filter are disposed on a filter tip distal to the distal anchor, wherein the vapor removal port comprises at least 70% of the surface area of the distal tip.

In one embodiment, the vapor delivery ports, the at least one vapor removal port, and the filter are disposed on a filter tip distal to the distal anchor, wherein the vapor removal port comprises at least 80% of the surface area of the distal tip.

In some embodiments, the filter comprises a porosity of a 300 micron pore size with an open area of 36-50%.

A method of delivering vapor to a uterus of a patient is provided, comprising inserting a portion of a uterine ablation device into the uterus of the patient, expanding a distal anchor of the uterine ablation device in the uterus, engaging a cervical collar of the uterine ablation device against an external os of the patient to pull the uterine ablation device proximally and place the distal anchor against an internal os of the patient, inflating a central balloon within the cervical canal to seal off the cervix from the uterus, and delivering a heated vapor to the uterus to ablate uterine tissue.

In some embodiments, the engaging step further comprises engaging a spring-loaded cervical collar against the external os.

A filtering tip of a vapor ablation device is provided, comprising a vapor delivery port adapted to receive vapor from a vapor delivery lumen and deliver the vapor near a target tissue, a vapor return port adapted to remove vapor to a vapor removal lumen, a filter disposed over at least the vapor return port, the vapor return port comprising at least 70% of an external surface area of the filtering tip so as to provide a vapor removal function if a portion of the filter is obstructed.

In some embodiments, the vapor return port comprises at least 80% of the external surface area of the filtering tip.

In another embodiment, the tip is substantially flexible.

In some embodiments, the vapor delivery lumen and the vapor removal lumen are substantially flexible.

In another embodiment, the vapor removal lumen is disposed around at least a portion of the vapor delivery lumen.

In some embodiments, the filter has a pore size of approximately 250 to 350 microns with an open area of approximately 36 to 50% to allow vapor to pass but prevent blood clots, tissue, and other bodily materials from passing.

In one embodiment, the vapor delivery port is disposed near a distal portion of the filtering tip, and the vapor return port comprises substantially the remainder of the surface area of the filtering tip.

BRIEF DESCRIPTION OF THE DRAWINGS

FIGS. 4A-4H illustrate methods of using a uterine ablation device.

DETAILED DESCRIPTION OF THE INVENTION

Figure 1A:
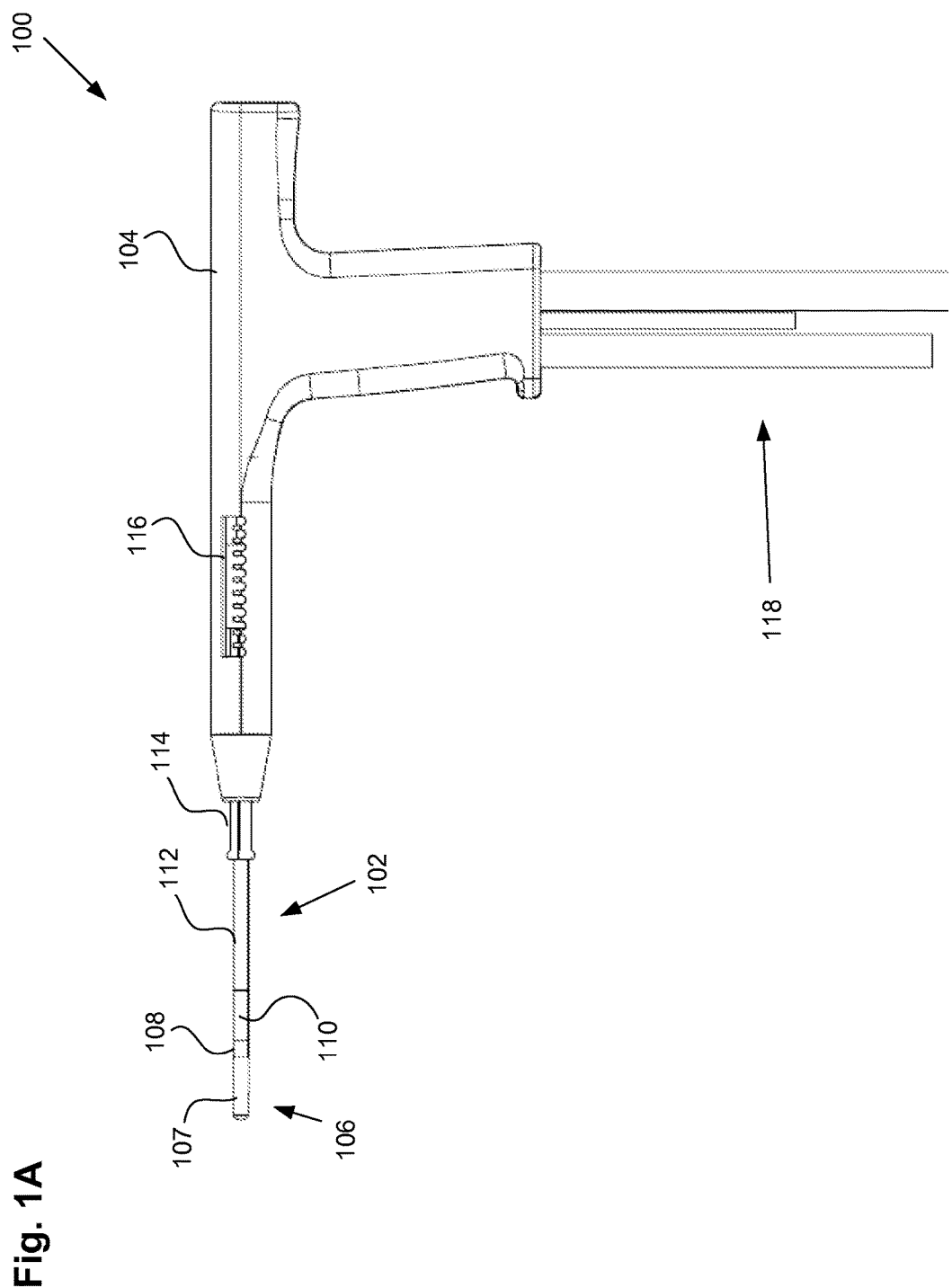
FIGS. 1A-1E illustrate one embodiment of a uterine ablation device.

FIG. 1A illustrates a uterine ablation device 100 sized and configured to access the endometrium of a uterus and to deliver a heated vapor to the uterus to ablate uterine tissue. The device can be configured to ablate and treat the endometrial lining of the uterus as an alternative to hysterectomy for treating menorrhagia or other uterine diseases. The device 100 can include shaft 102, handle 104, distal tip 106, vapor ports 107, distal anchor or distal balloon 108, central or sealing balloon 110, proximal or positioning balloon 112, cervical collar 114, cervical measurement 116, and connection lumens 118, which can couple the uterine ablation device to a control system (not shown) comprising a computer, a vapor generation system, and mechanisms configured to inflate and deflate the balloons as well as control the delivery and removal of vapor from the device. Handle 104 can be an ergonomic handle and can include features and controls for using the device (e.g., buttons, levers, indicia for providing feedback for depths of insertion, valves, etc), including features for controlling inflation of balloons 108, 110, and 112, and for controlling the delivery and removal of heated vapor from the device. It should be noted that in some embodiments, the distal anchor comprises a balloon, but in other embodiments, the distal anchor comprises an expandable anchor or expansion mechanism, such as expandable frames, filters, nets, or cages. For purposes of this disclosure, however, the distal anchor may be referred to as a distal anchor or as a distal balloon.

Cervical collar 114 and cervical measurement 116 can provide a mechanism for properly inserting the uterine ablation device the correct distance into the patient's uterus. The cervical collar is configured to abut an external os of the cervix to prevent advancing the device too far and puncturing the uterine wall. Since uterine ablation procedures are typically conducted without the use of video or real time imaging, the cervical collar can provide a palpable indicator of the location of the external face of the cervix to prevent damage to the uterus from over-insertion. For example, prior to a uterine ablation procedure, a physician can measure the distance from the external os of the cervix to the internal os of the uterus (e.g., the physician can measure the length of the cervix) and compare that length with the total overall length from the external os of the cervix to the interior fundus of the uterus. Next, the physician can adjust cervical measurement 116 to coincide with the measured cervical length. Adjusting cervical measurement 116 causes cervical collar 114 to slide axially along shaft 102, either lengthening or shortening the distance from distal tip 106 to the cervical collar 114. Thus, the cervical collar 114 can be adjusted based on the cervical measurement to aid in positioning the distal tip of the uterine ablation device in the proper position within the uterus (e.g., just past the internal os of the cervix, or in some embodiments, approximately 1 cm past the internal os). When the cervical collar has been properly positioned along the shaft of the device, the physician can insert the device into the patient until the cervical collar touches the external os of the cervix, thereby placing the distal tip of the device within the uterus of the patient without puncturing the distal wall of the uterus.

The cervical collar 114 can be configured as a cylindrical shape and can comprise a soft, low durometer material such as silicone that can slide along the shaft to circumferentially surround the positioning balloon 112, but can expand easily when the positioning balloon is inflated. The distal portion of the cervical collar can have a variety of shapes to provide an atraumatic, non-penetrating surface. In some embodiments, the cervical collar does not surround the entire shaft but instead has a curved/hooked shape and can be made from a material such as stainless steel, polyethylene, or biocompatible material. In other embodiments, the cervical feeler can include a T-shape, a semi-circular footing, or a rounded shape. In some embodiments, more than one cervical feeler can be used so as to provide for multiple places of contact with the external os of the patient. Also, it may be preferable for the physician to pick and identify one spot on the external cervical face to make his internal fundal and cervical length measurements. This is because the cervix may not present itself as a normal, horizontal surface. As an example, picturing the cervix as a clock face, the physician may choose a location at 3 o'clock on the cervix. It may be preferable to have the cervical feeler attached to the cylindrical marking device on a rotatable collar so that the surgeon can ensure that the feeler hits the same reference point.

The balloons described herein can be any type of flexible balloon, such as rubber, latex, urethane, silicone, PET, LDPE, parylene, nylon, PE, combinations of these polymers, or can be manufactured from any other suitable material as known in the art.

Shaft 102 can be configured to deliver a heated vapor from a remote vapor source (not shown) through the device and out of vapor ports 107 in distal tip 106. The shaft can also be configured to return vapor that has exited the device, including bodily fluids, uterine materials, and condensate back through the vapor ports and into the shaft. In FIG. 1A, vapor ports 107 can include both vapor delivery and vapor return ports. In some embodiments, vapor delivery ports are separate and distinct from the vapor return ports, and in other embodiments, the same ports are used for both vapor delivery and vapor return. The vapor delivery ports are configured to provide an even distribution of heated vapor through a cavity or a balloon, an inflatable membrane or other porous structure, and may comprise small lumens or holes on the end of the shaft. The vapor return ports, in contrast, are configured to return used vapor and condensate, and may comprise larger slots to prevent blood, tissue, etc from blocking or clogging the return lumen. In some embodiments, as will be discussed in detail below, the entire distal tip 106 of the device, including vapor delivery and vapor return ports, can be covered with a mesh so as to filter any materials that may clog or obstruct the device.

Referring still to FIG. 1A, uterine ablation device 100 is shown in a collapsed delivery configuration, with distal balloon 108, sealing balloon 110, and positioning balloon 112 deflated to reduce the cross sectional diameter of the device and can be 6 mm in diameter during insertion or smaller. When the device is in the delivery configuration, the reduced profile allows for easier access to through the vagina, cervical canal, and cervix to gain access to the uterus, and provides reduced patient discomfort during insertion. In some embodiments, the outer dimensions of the uterine ablation device are such that introduction of the device into the uterine cavity can be achieved without the need for mechanical or pharmacological dilation of the os prior to device introduction.

Figure 1B:
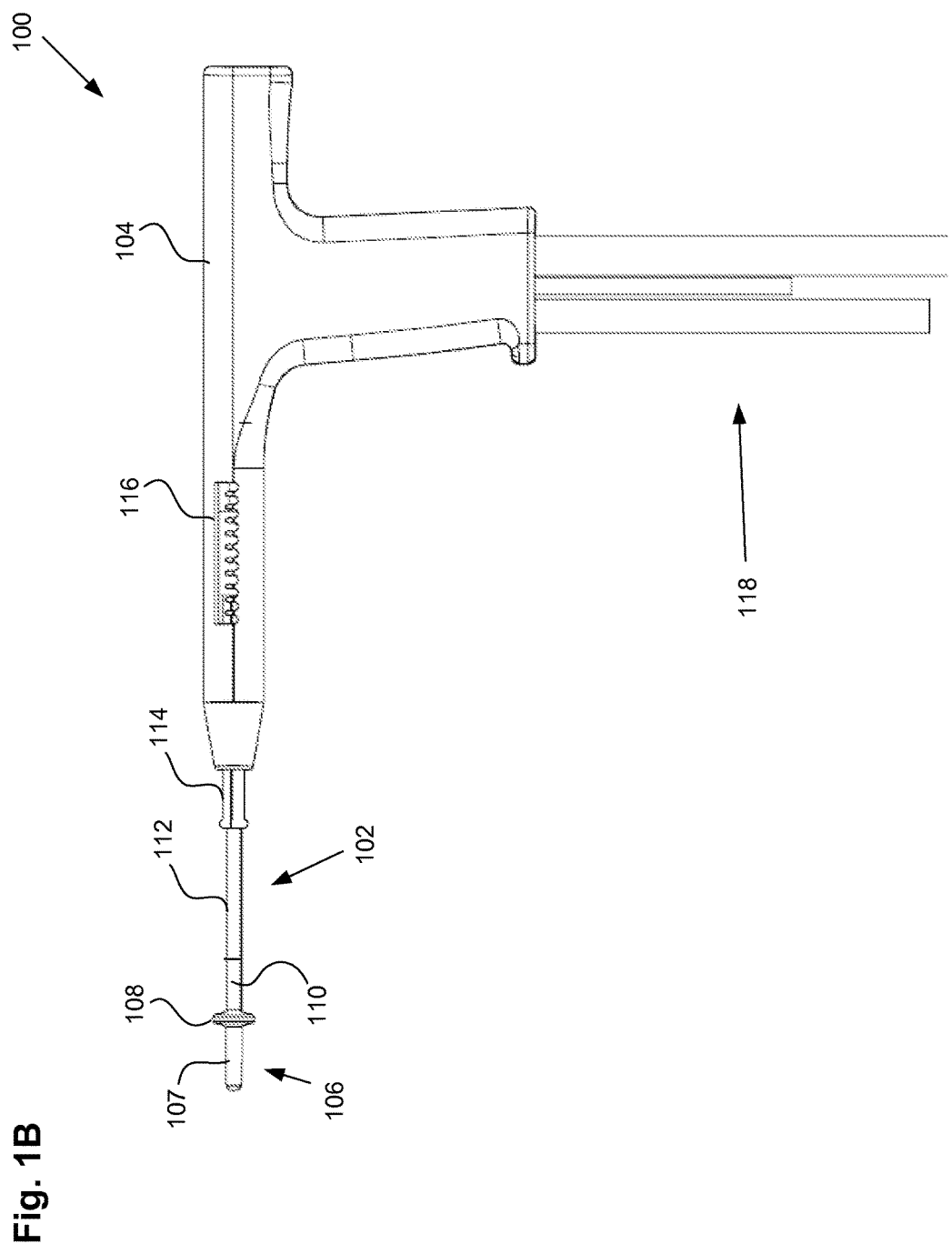

FIG. 1B illustrates the uterine ablation device 100 of FIG. 1A with distal balloon 108 inflated. As shown the distal balloon 108 can comprise a disk or donut-like shape, so as to extend radially outward enough to provide adequate positioning within the uterus, while remaining narrow enough so as to block a minimal amount of tissue an not interfere with the vapor therapy. In some embodiments, the distal balloon can comprise a length along shaft 102 of approximately 3 to 10 mm and can comprise a diameter of approximately 13 to 16 mm. In other embodiments, the distal balloon can comprise other shapes, including spherical, tubular, or football shaped balloons. In some embodiments, the distal balloon can be replaced with a mechanical expansion mechanism such as flanges, hinges, frames, cages, filters, or nets that can be expanded by push-pull mechanisms of the outer shaft, or rotation of the outer shaft, in relation to an inner shaft connected to the mechanical expansion mechanism.

The distal balloon 108 can be inflated with a fluid, such as saline, or alternatively, can be inflated with air or gas. The distal balloon can be inflated with a room temperature medium, a cooled medium, or alternatively, a heated medium. In one embodiment, the positioning balloon can be filled with an echogenic medium. In another embodiment, the positioning balloon can be inflated with a saline and air bubbles mixture to allow for greater echogenicity via ultrasound imaging. In some embodiments, the positioning balloon includes a conductive coating to allow for heat transfer from the heated vapor through the conductive coating to the tissue. The positioning balloon can be molded or formed with structural grooves, ridges, or indentations that allow for vapor or heated materials to flow around the positioning balloon to treat the tissue in contact and proximal to the positioning balloon. The distal balloon is configured to be positioned just distal (approximately 1 cm) from the internal cervical os. This area of treatment just distal to the internal cervical os is generally referred to as the lower uterine segment.

The distal balloon can typically be inflated to a pressure of approximately 20 to 30 psi. With the distal balloon inflated to this inflation pressure, the axial force required to pull out the device from the uterus can range from 2 to 5 lbs. of force. In some embodiments, this inflation pressure is the pressure required to prevent accidental removal of the inflated balloon from the uterus, through the cervix.

Figure 1C:
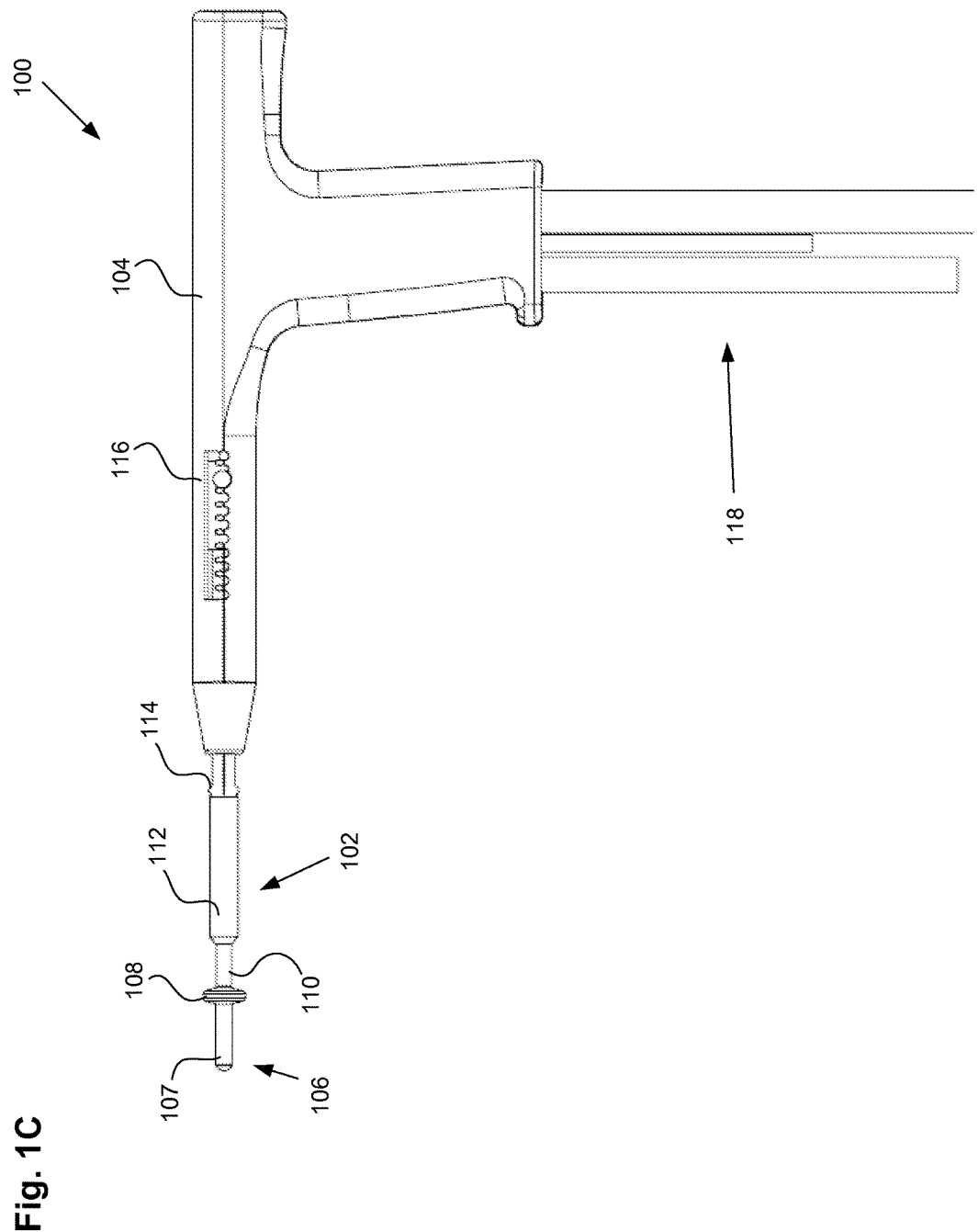
Figure 1D:
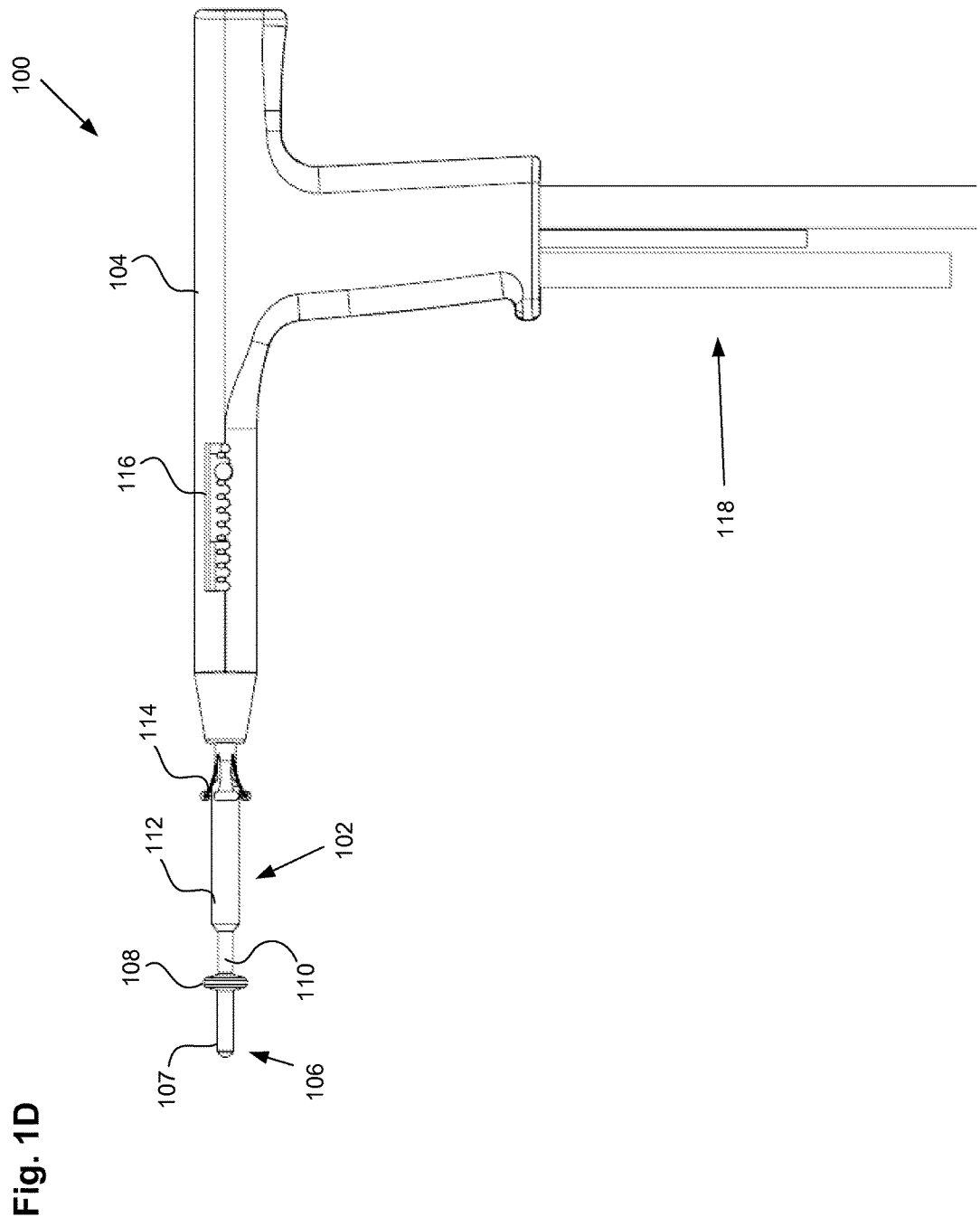

FIGS. 1C-1D illustrate the uterine ablation device 100 of FIGS. 1A-1B with the positioning or proximal balloon 112 also inflated. As shown in FIGS. 1C-1D, both the distal balloon 108 and the positioning balloon 112 are inflated. The positioning balloon can also be inflated with a fluid, such as saline, or alternatively, can be inflated with air. In some embodiments, the proximal balloon can comprise a length along shaft 102 of approximately 50 mm to 70 mm. In another embodiment, the proximal balloon comprises a length along the shaft of approximately 40 mm to 90 mm. The length of the proximal balloon, and its distance along the shaft from distal balloon 108, ensures that when inflated, the proximal balloon will span the patient anatomy from at least a portion of the cervix, past the external os, and into the vagina. The proximal balloon can be inflated with a room temperature medium, a cooled medium, or alternatively, a heated medium. In FIG. 1C, the positioning balloon 112 is inflated, but the cervical collar 114 is positioned proximally from the positioning balloon so that inflation of the balloon does not expand the collar. In FIG. 1D, however, the cervical collar 114 is advanced distally along shaft 102 so as to partially surround positioning balloon 112. In this embodiment, when the proximal balloon is expanded, the cervical collar 114 is configured to expand radially outwards with the balloon, as shown.

Figure 1E:
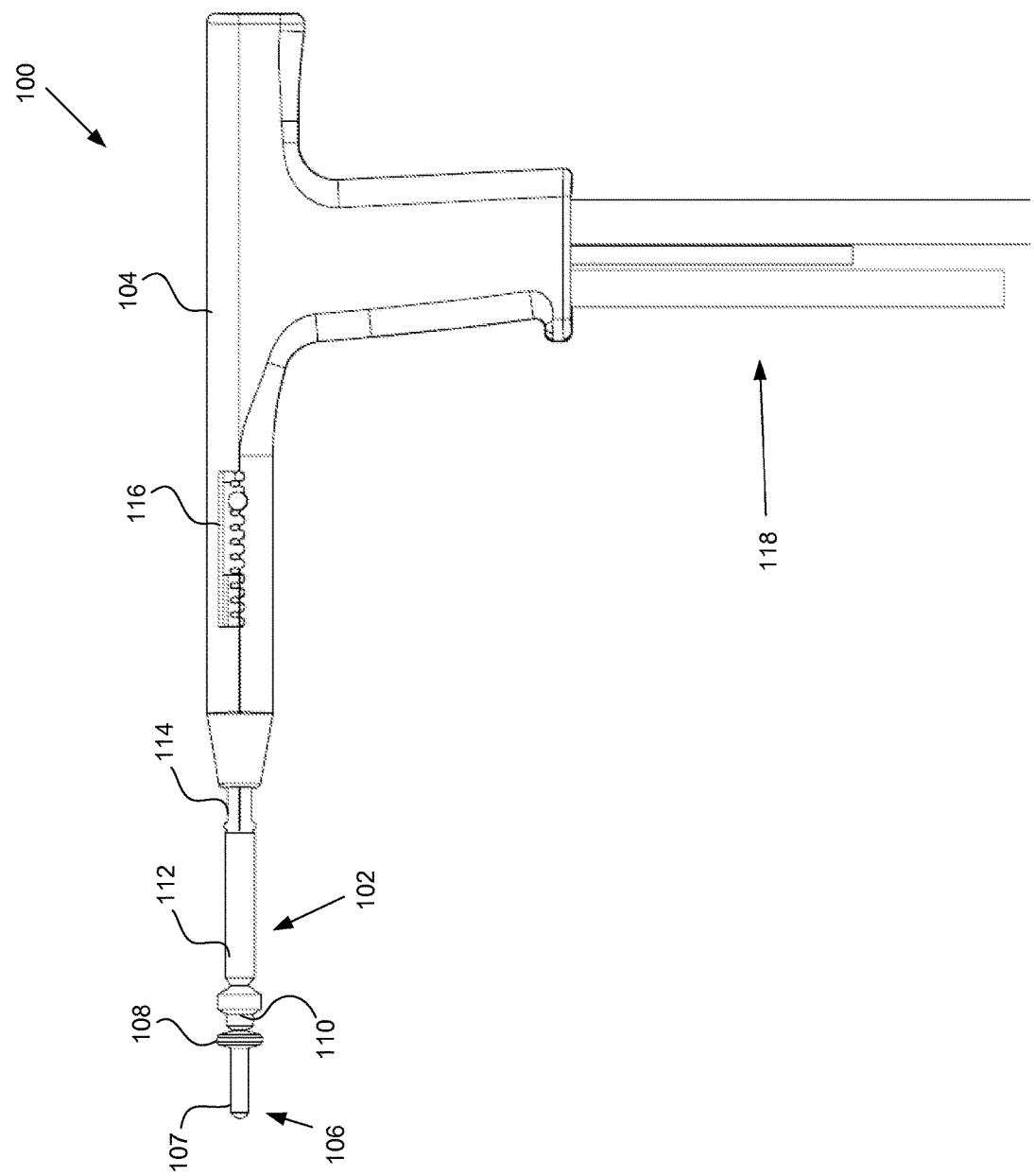

FIG. 1E illustrates the uterine ablation device 100 of FIGS. 1A-1D with all three balloons inflated, including distal balloon 108, central sealing balloon 110, and positioning balloon 112. The central balloon can be inflated with a fluid, such as saline, or alternatively, can be inflated with air. The positioning balloon can be inflated with a room temperature medium, a cooled medium, or alternatively, a heated medium. In some embodiments, the central sealing balloon comprises a length along shaft 102 of approximately 15 mm to 25 mm. The central balloon can be disposed on the shaft between the distal balloon or anchor and the proximal balloon. In some embodiments, the central balloon is adjacent to both the distal balloon and the proximal balloon. In other embodiments, there is a small gap or space between one or more of the balloons. The length and position of the central balloon on the shaft ensures that when inflated, the central balloon seals the cervix off from the uterus near the internal os, but the balloon does not extend into the uterus or into the vagina of the patient. The central and proximal balloons can comprise any diameter, but preferably should have a diameter large enough to be able to engage the walls of the cervix and/or the vagina in the average female patient.

Figure 2:
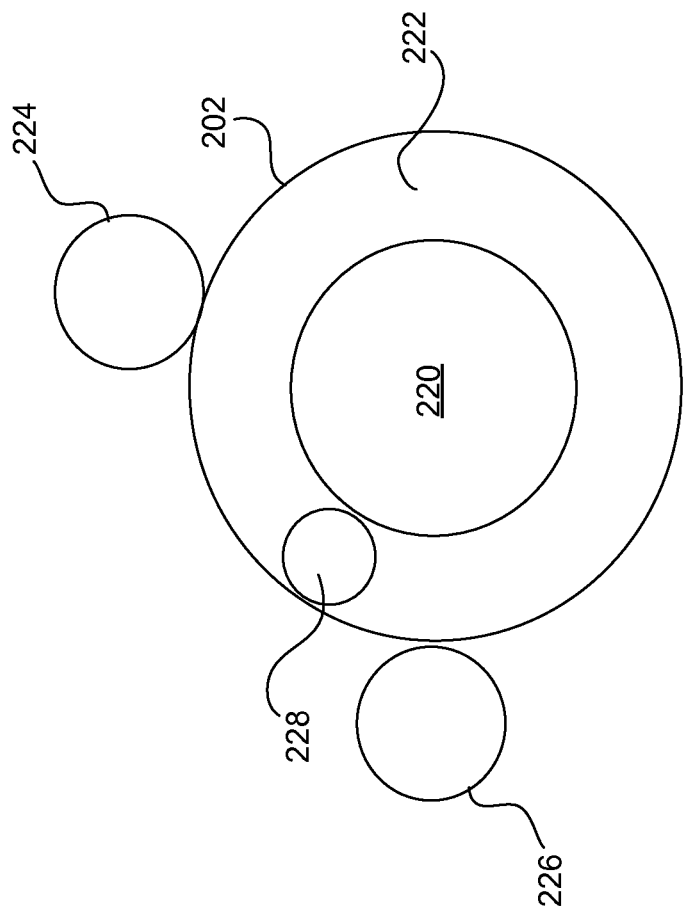
FIG. 2 illustrates a cross sectional view of a shaft of a uterine ablation device.

FIG. 2 illustrates a cross sectional view of shaft 202, which can correspond with shaft 102 of FIGS. 1A-1E above. The shaft can include vapor delivery lumen 220, vapor return lumen 222, and balloon inflation lumens 224, 226, and 228 corresponding to each of the distal balloon, sealing balloon, and positioning balloon described above.

Vapor delivery lumen 220 can be a central lumen within shaft 202 configured to deliver a heated high-quality vapor through the uterine ablation device to tissue. The vapor delivery lumen can be coupled to a vapor source, and can transport vapor from the vapor source to the distal tip of the device and out towards tissue via vapor delivery ports. The vapor delivery lumen can be concentrically placed within vapor return lumen 222, as shown. In some embodiments, the positions of vapor delivery lumen and vapor return lumen can be switched. balloon inflation lumens 224, 226, and 228 can be configured to inflate and deflate the three balloons described above. It should be understood that the individual inflation lumens can be used for other balloons and other devices in additional embodiments. In some embodiments, one or more balloon inflation lumens are positioned external to shaft 202, and in other embodiments, one or more balloon inflation lumens are positioned within shaft 202, such as within vapor return lumen 222 as shown in FIG. 2. In one embodiment, a sensor (such as a fiber optic sensor) or thermocouple lead can be placed through an inflation lumen along the length of the shaft so as to position the sensor on or near the distal tip of the device.

In additional embodiments, lumens 220 and 222 can be off-center, or alternatively, the lumens need not be concentric and can be disposed side by side. In some embodiments, the shaft 202 can be surrounded by an additional lumen containing insulation to prevent damage to tissue that comes into contact with the shaft during vapor delivery. The shaft can be made from a variety of rigid and flexible materials such as stainless steel, titanium, Nitinol®, PEEK, polycarbonate, PET, and polyimide. In some embodiments the shaft may comprise multi-lumen extrusions for ease of assembly.

Figure 3C:
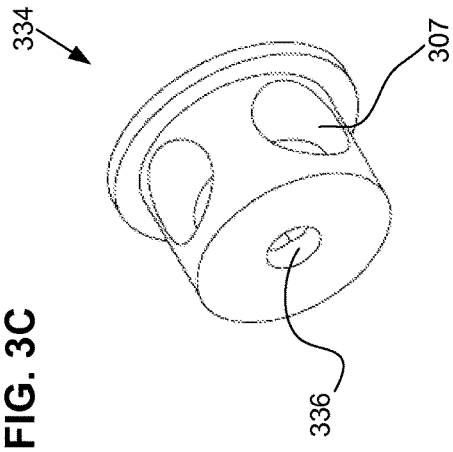
FIGS. 3A-3D illustrate one embodiment of a distal filter tip of a uterine ablation device.
Figure 3D:
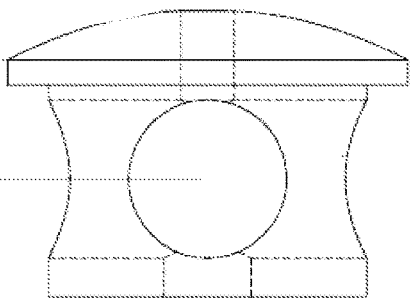
Figure 3A:
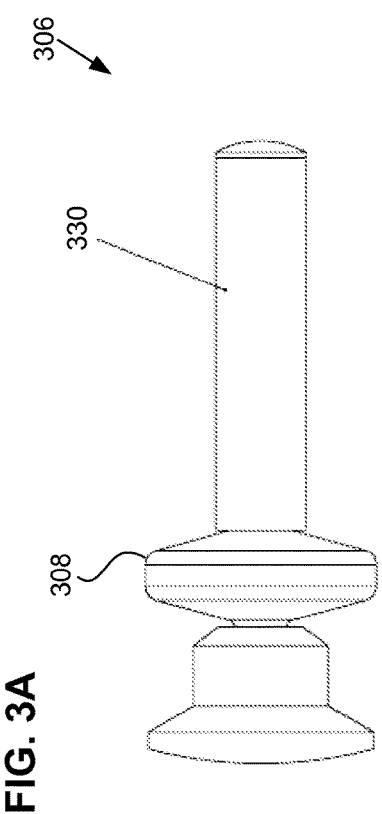

FIGS. 3A-3D illustrates one embodiment of a distal tip 306, corresponding to distal tip 106 of FIGS. 1A-1E. FIG. 3A illustrates a side view of distal tip 306, including a filter or mesh 330 configured to keep blood and tissue out of the return lumen of the shaft. The mesh 330 can cover the vapor ports, vapor return ports, vapor delivery lumen, and vapor return lumen, but still allow for the delivery and return of vapor to a patient. Additionally, the mesh structure can help protect and maintain in position internal components such as the vapor delivery elements and measurement devices such as pressure and temperature sensors within the tip. In some embodiments, the mesh can be made from a fluoropolymer, PET, nylon, or PE material. In a further refinement, the mesh can be provided with a certain porosity and geometry to create filter made from PET with about a 300 micron pore size (with an open area of 36-50%) to create an optimum flow through for vapor return with the ability to reduce the amount of particulates and other bodily materials from entering the return lumen. In some embodiments, the distal tip is rigid, and in other embodiments the tip incorporates flexibility so that it conforms to the anatomy of the uterine cavity to prevent damage or perforation of the uterine wall, while maintaining column strength sufficient to allow easy introduction through the os, into the uterine cavity. In another embodiment, the filter can be made to expand in the uterine cavity to increase the amount of surface area available for filtering material from the uterine cavity. This expansion can be created be mechanically advancing the distal end of the filter tip, rotating the outer shaft and unrolling the distal filter tip, or expanding and stretching corrugations in the filter tip.

Figure 3B:
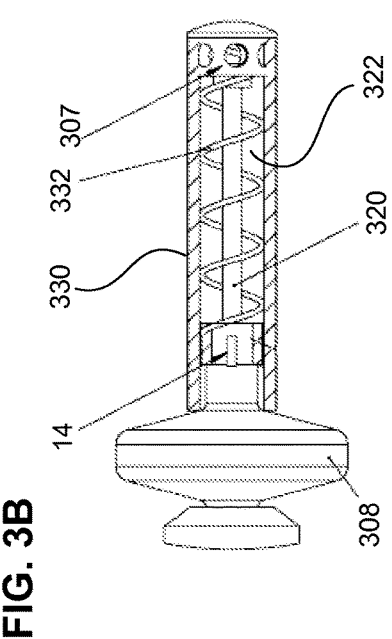

FIG. 3B is a cross sectional view of the distal tip of FIG. 3A, showing the internal elements of the distal tip. As shown, the distal tip can incorporate supportive elements 332, such as coils or ribbons, to maintain its cylindrical shape and support the mesh in place. As shown in the cross sectional view, vapor delivery lumen 320 can be positioned centrally to the distal tip, and surrounded by supportive elements 332 and mesh 330. The vapor delivery lumen 320 can terminate at vapor ports 307, which are configured to spray or deliver vapor from the distal tip of the device. The remaining volume within the distal tip can comprise vapor return lumen 322, which, as described above, can be a concentric lumen to vapor delivery lumen 320. Maximizing the surface area available for the vapor return lumen can prevent clogging during operation of the device. Thus, in some embodiments, the vapor delivery ports can comprise as little as 10% of the surface area of the distal tip, and the vapor return ports or vapor return lumen can comprise as much as 80% of the surface area of the distal tip and in some embodiments higher surface areas of up to approximately 95%.

In some embodiments, the distal tip contains nozzles for delivering the vapor in a spray pattern. The plurality of nozzles or ports can help prevent obstruction of the vapor source by the surrounding tissue, such as in cases where the device embeds partially into the uterine wall. In some embodiments, separate vapor ports are coupled to the delivery and return lumens. The vapor delivery ports can comprise slits, holes (as shown in FIG. 3B), or various other nozzle shapes configured to deliver a heated vapor from the ablation device.

FIGS. 3C and 3D illustrate one embodiment of a split chamber tip 334 having vapor delivery ports 307 that can be used at the distal end of distal tip 306. Slot 336 can be configured to receive the vapor delivery lumen described above. As shown in the cross-sectional view in FIG. 3D, the split chamber tip 334 can include a chamber 338 within the tip to aid in dispersing the vapor prior to reaching vapor delivery ports 307. The split chamber tip can be constructed from a porous mesh made from PET or other polymer, metallic screen, or fibers to prevent debris from entering the vapor probe.

In another embodiment, the distal tip of the device can reside within an inflatable balloon or membrane that is affixed to the shaft. Vapor that exits the distal tip can inflate the balloon that contacts the inner lining of the body cavity or uterus. The vapor ports in conjunction with the return lumen provide a continuous flow of heated vapor to the balloon or membrane while condensate and excess pressure is relieved through the distal tip and return lumen. In addition, heated vapor can be supplied preferentially and separately to the distal balloon to provide a specific heating regime to the lower uterine area near the internal os.

Compartmentally, different heating protocols can be configured with multiple balloon configurations within the bodily cavity depending upon the application, tissue mass, and the desire to minimize or maximize the amount of ablation within a certain target area of the body. As an example, separate balloon compartments can be configure to preferentially inflate in the corneal areas of the uterus where the amount of thermal energy required would be less than required in the corpus or fundus of the uterus. Conversely, different balloons or membranes can be filled with cooling media (fluid or gas) that serves to preserve that area of tissue from thermal injury. As an example, the sealing balloon and proximal positioning balloon (from the above figures) can be supplied with cooling media to protect the cervical area while the uterine cavity balloon is filled with vapor and distal balloon supplied with less vapor or intermittent vapor to reduce the amount of the thermal energy supplied in this area of the body.

Figure 4A:
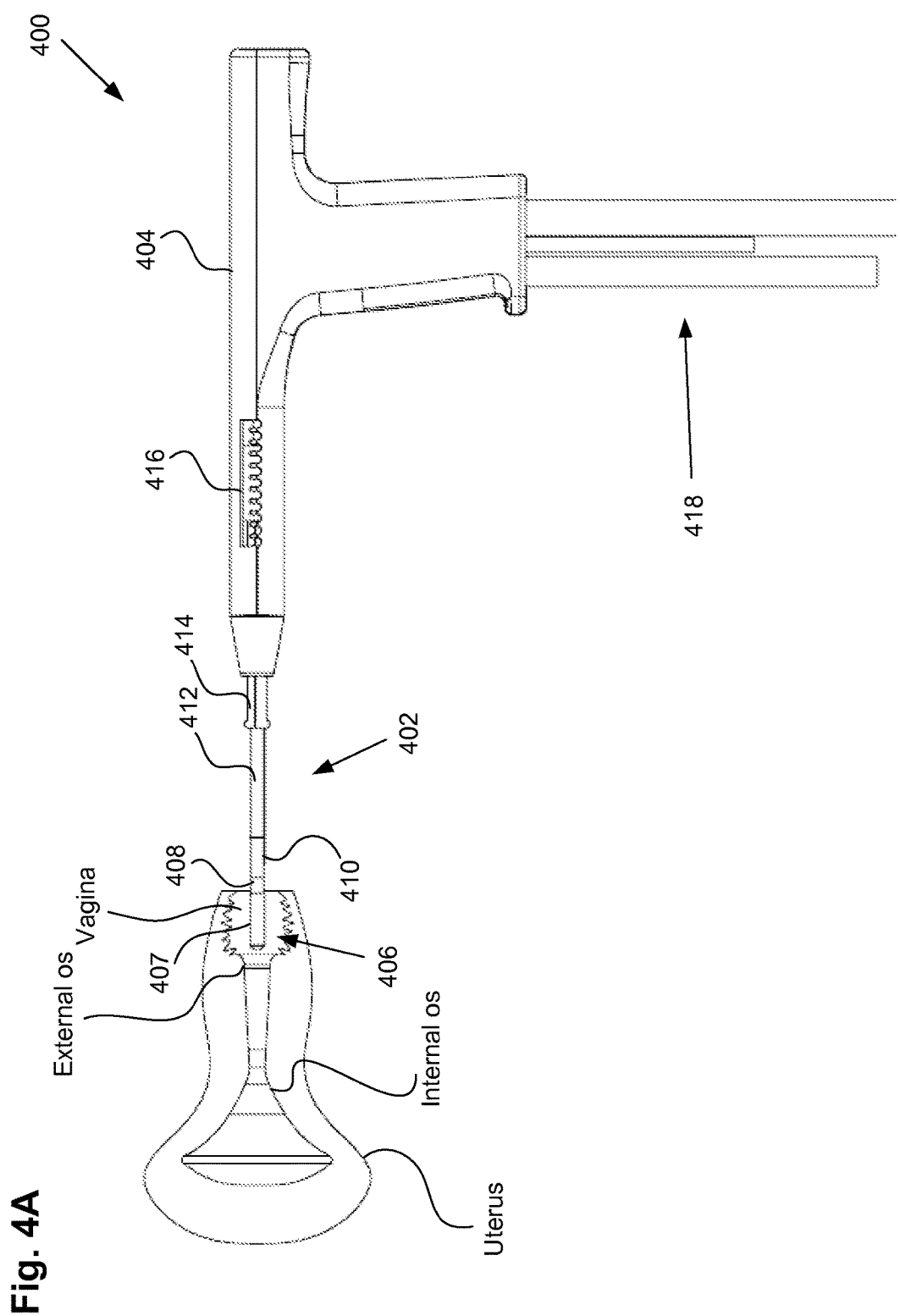

A method of using the uterine ablation device will now be described with respect to FIGS. 4A-4C. Uterine ablation device 400 of FIGS. 4A-4C can be the uterine ablation device described above. Prior to using the device, a physician can measure the length of the patient's cervix, or a distance from a reference point in the vagina to the fundus, and adjust cervical measurement 416 on device 400 to correspond to the measured or estimated cervical length. This, in turn, adjusts the position of cervical collar 414 along shaft 402 to prevent over advancement the ablation device and perforating the uterus. Referring to FIG. 4A, uterine ablation device 200 can be arranged in a delivery configuration with all three balloons 408, 410, and 412 deflated and inserted into the vagina approaching the external os of the cervix.

Next, referring to FIG. 4B, the distal tip 406 of the ablation device can be inserted past the external os into the cervical canal, and past the internal os of the patient to gain access to the uterus. In one embodiment, the distal balloon 408 is positioned within the uterus distal to the internal os, the sealing balloon 410 is positioned at or proximal to the internal os and extending into the cervical canal, and the positioning balloon 412 is positioned within the cervical canal and extending proximally into or towards the vagina. In some embodiments, as shown in FIG. 4B, cervical collar 414 abuts the external os of the cervix, preventing further advancement of the device and preventing perforation of the uterine cavity. Adjusting the distance of the cervical collar to the distal tip based on a cervical measurement can ensure proper positioning of the distal tip of the device within the uterus, such as approximately 1 cm distal to the internal os.

Figure 4C:
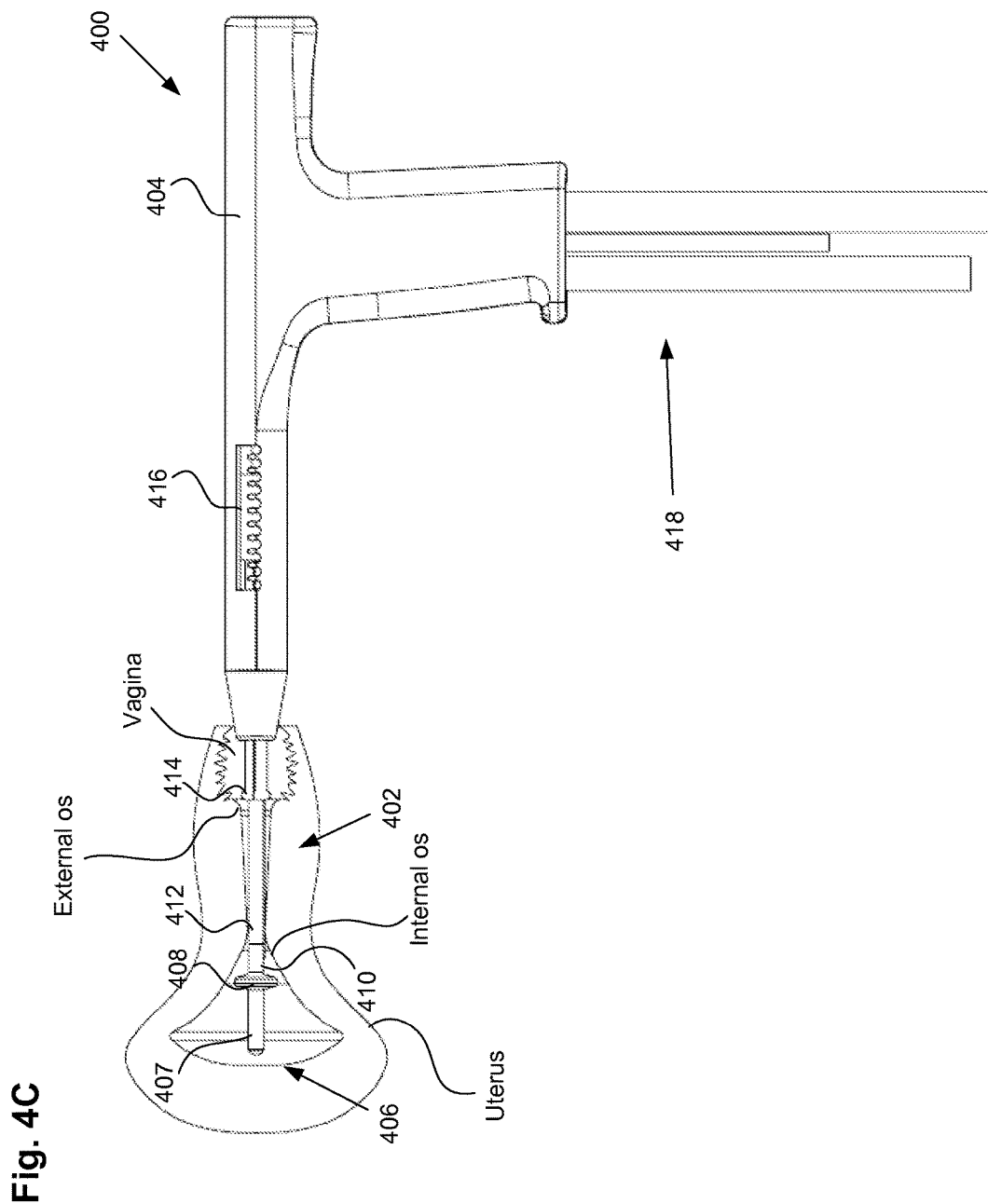

Referring now to FIG. 4C, once distal tip 406 of the ablation device is disposed within the uterus, just distal to the internal os, the distal balloon 408 can be inflated to the desired pressure. In some embodiments, the balloon can be inflated to a pressure of up to approximately 20 to 30 psi so as to prevent accidental withdrawal of the ablation device from the uterus. It should be noted that at this point in the method, the distal balloon is positioned slightly past the internal os of the cervix. Inflation of the distal balloon can later serve as an anchor to prevent the device from sliding proximally out of the uterus.

Figure 4D:
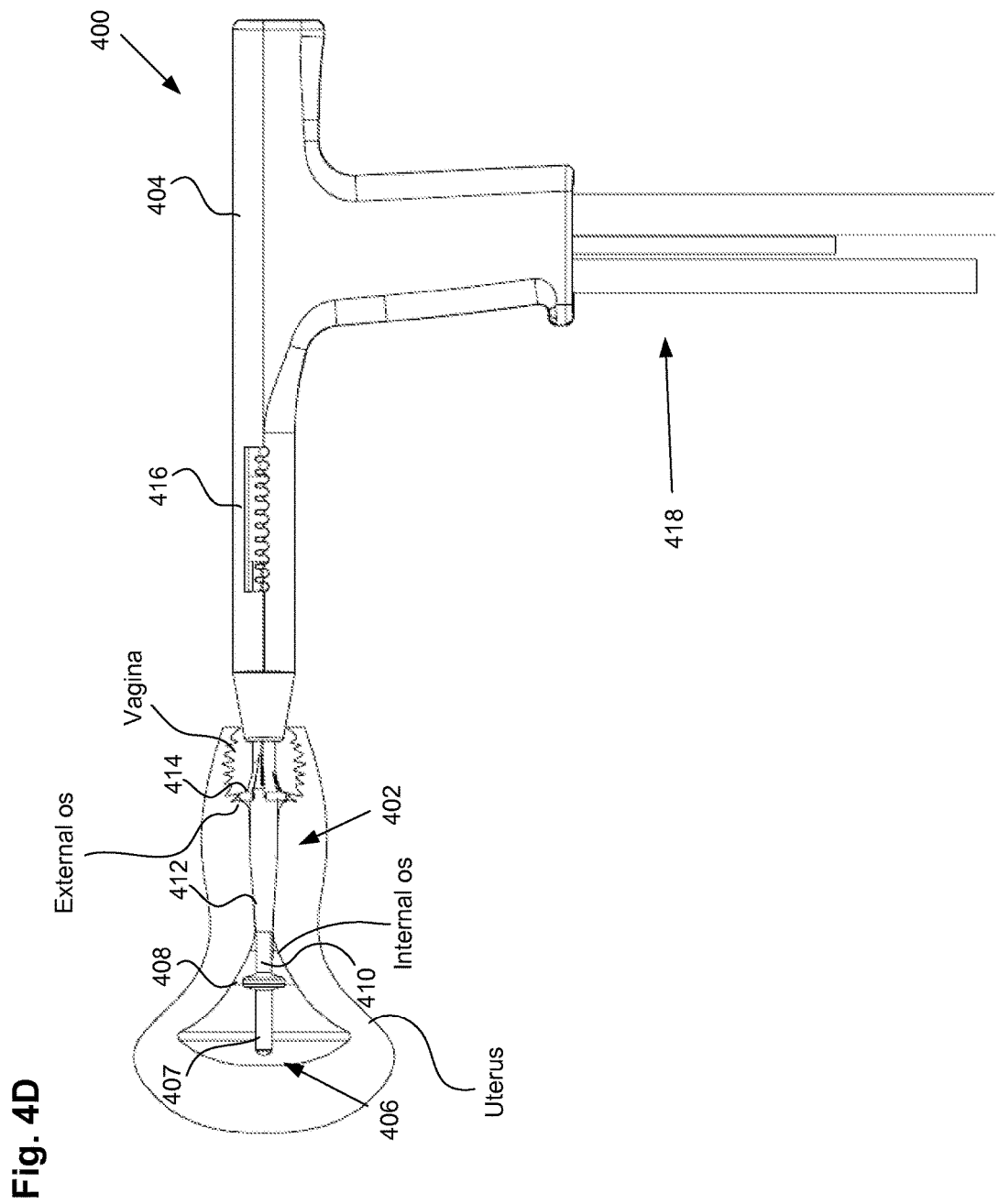

Referring now to FIG. 4D, after inflating the distal balloon, proximal balloon 412 can be inflated to cause the device to assume the positioned configuration, as shown in FIG. 4E, with the distal balloon 408 full seated against the internal os and the positioning or proximal balloon 412 expanded within the cervix and extending past the external os into the vagina. It should be noted that in FIG. 4D, the proximal balloon is only partially inflated, and the distal balloon is still a short distance away from the internal os of the cervix. As the proximal balloon is inflated, the balloon can expand outwardly from the cervix into the relatively unconstrained space of the vagina, which creates a compression force that pulls the device and distal balloon 408 proximally to engage against the interior portion of the internal os (also known as the cervical ostium or cervical os). It should also be noted that in FIG. 4D, as the proximal positioning balloon 412 expands, the cervical collar 414 is adapted to expand radially to allow expansion of the balloon, while maintaining contact with the cervix to prevent over insertion.

FIG. 4E illustrates the distal balloon fully seated against the internal os, and shows positioning balloon fully inflated and spanning the distance from a portion of the cervix to a portion of the vagina. Inflation of the positioning balloon from within the cervix out into the vagina is critical for positioning the uterine ablation device properly within the patient. As the balloon expands outwards into the vagina, it can assume a "wedge" shape, which causes the proximal device movement indicated by arrows 440 to seat the distal balloon against the internal os. The distal balloon can have a sealing effect against the internal os as the positioning balloon pulls it proximally. One advantage of the proximal positioning balloon is to standardize the amount of compression forces from patient to patient and physician to physician. In some embodiments, the compression forces range from 0.5 to 3 lbs. This consistency can ensure that a minimum amount of compression is applied for each procedure, and can eliminate the risk of one physician pulling too hard and extracting the device from the patient when the distal balloon is inflated. In one embodiment, the positioning balloon is inflated as high as 10 psi to position the device to pull the device proximally and seat the distal balloon against the internal os.

Figure 4F:
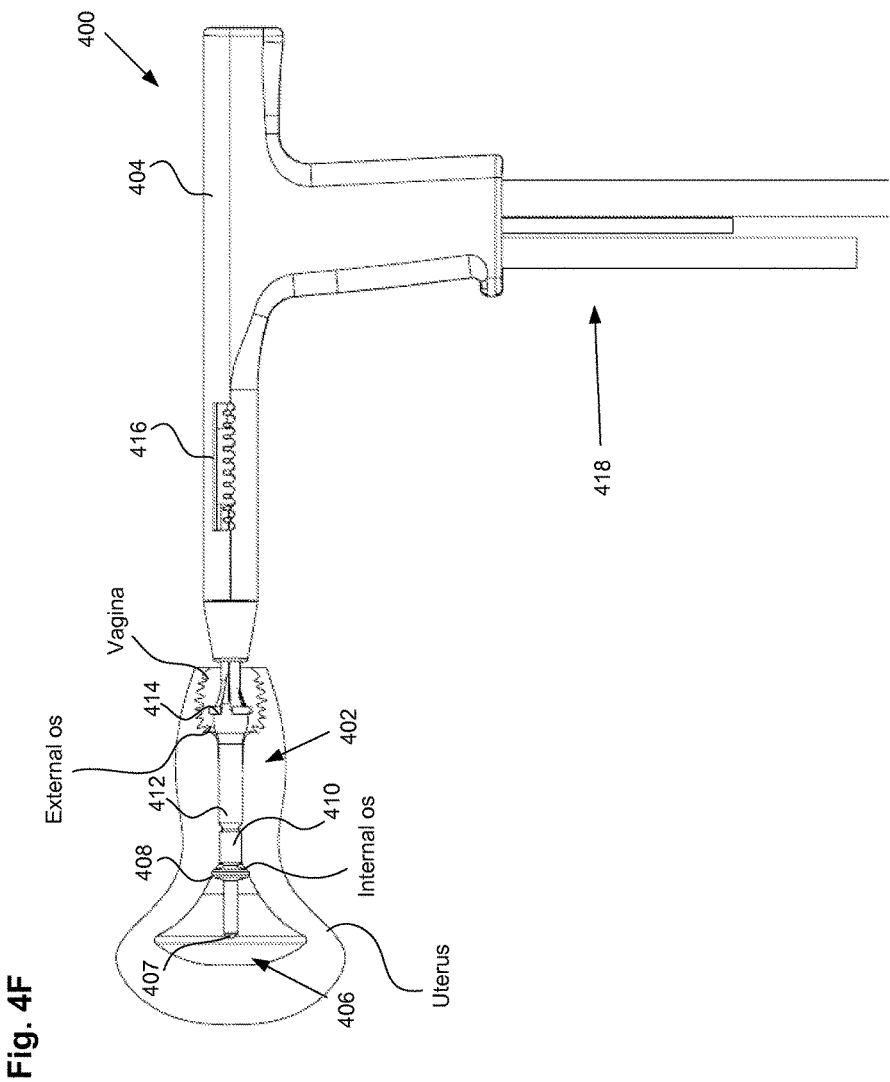

Referring now to FIG. 4F, when the ablation device, more specifically the distal balloon, is positioned against the cervical os as in FIG. 4E, sealing balloon 410 can be inflated to seal the cervical canal off from the uterus. The sealing balloon 410 is configured to seal off the uterus from the cervical canal and vagina, such as proximally to the internal os, so as to prevent leakage of vapor back into those sensitive portions of the patient's anatomy. In this figure, the sealing balloon is shown as cylindrically-shaped, but it may be advantageous to have the sealing balloon with variable geometry (e.g. with radial projections, pear-shape, bulbous proximal end) to more firmly engage the cervical canal or external os of the cervix. In one embodiment, the sealing balloon is inflated as high as 7 psi to seal off the uterus from the rest of the anatomy. The system described herein can provide for triple-redundant sealing; the distal balloon 408 against the interior surface of the internal os, the sealing balloon 410 against the interior surface of the interior os as well as along a portion of the interior surface of the cervical canal, and the positioning balloon 412 against a portion of the interior surface of the cervical canal, the exterior os, and a portion of the vagina. This arrangement provides for maximum safety for the patient as well as increased accuracy in positioning the device prior to vapor delivery and ablation.

Figure 4G:
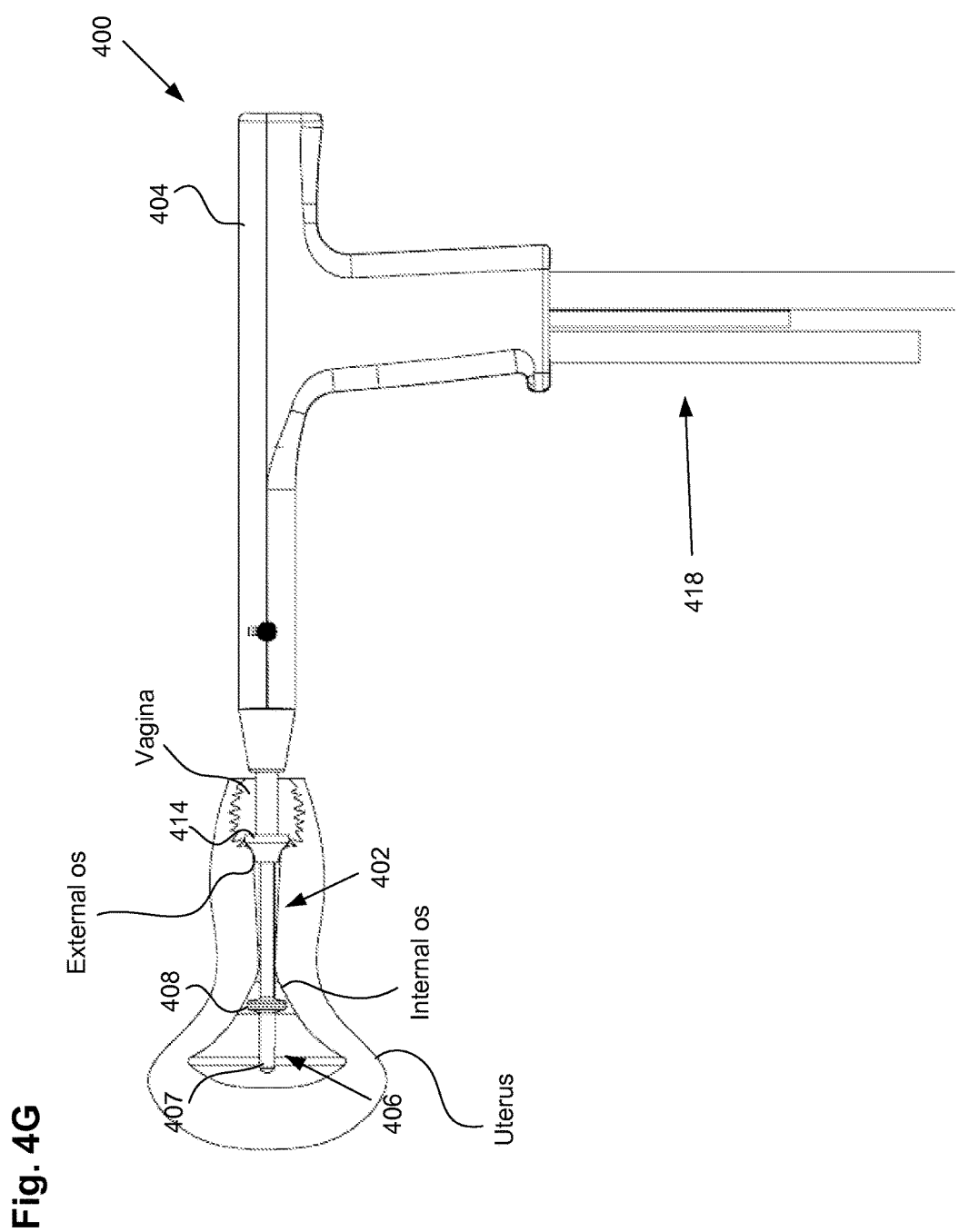
Figure 4H:
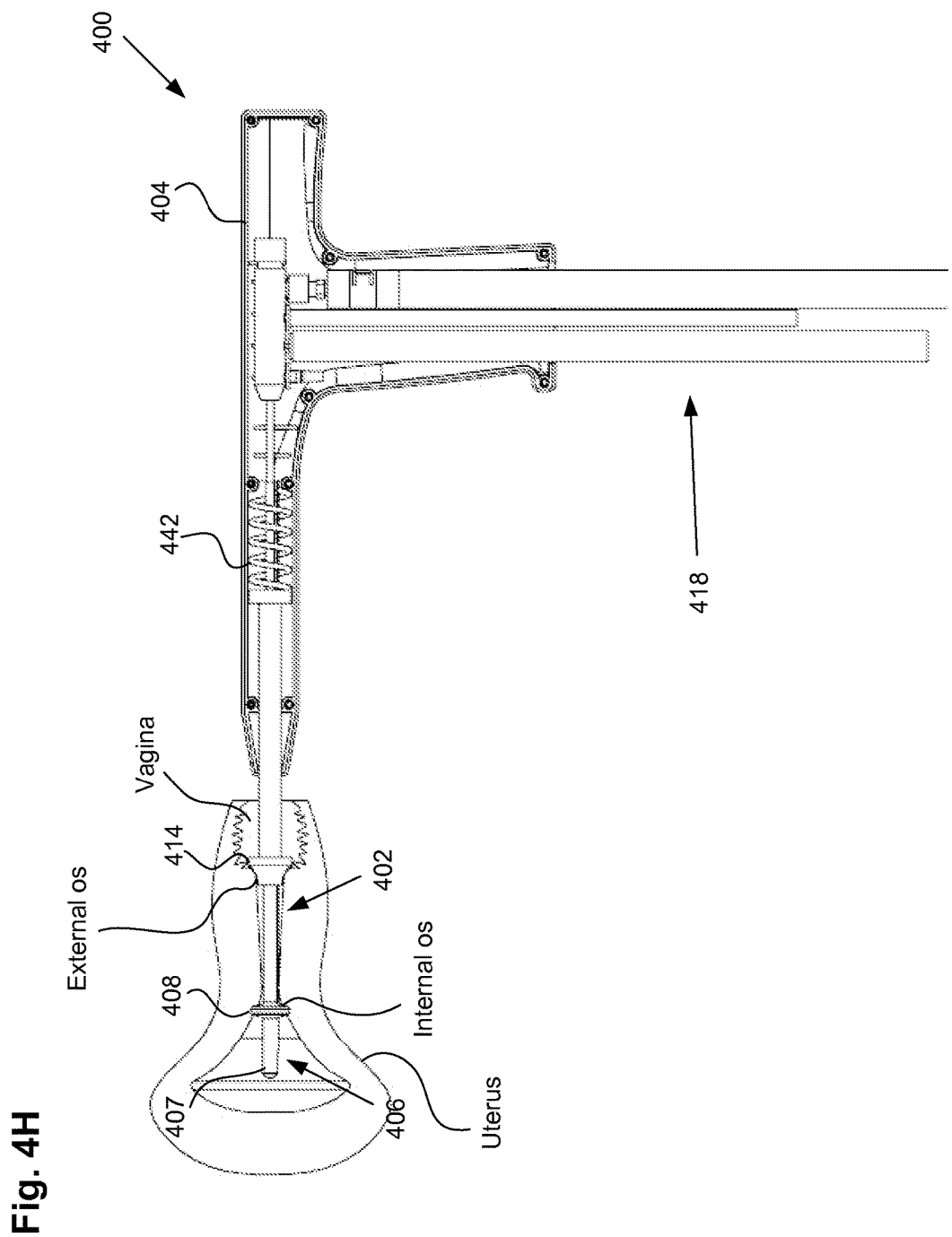

In another embodiment, referring now to FIGS. 4G-4H, the proximal balloon function can also be accomplished by a non-expandable cervical collar that is spring loaded. For example, in FIG. 4G, the distal tip of the ablation device can be positioned within the uterus, and the distal balloon or anchor 408 can be inflated or expanded distally to the internal os, as described above, and the cervical collar 414 can be placed in contact with the external os. As shown, the cervical collar in this embodiment can include a non-expandable, wedge shaped collar. In other embodiments, the cervical collar can be expandable. However, the collar should be sized and shaped so as to engage the external os and prevent the cervical collar from fully entering the cervix. Referring to FIG. 4H, the device can include a spring 442 or other force mechanism (e.g., a mechanical ratchet, a piston, a motor, etc) configured to apply force to the cervical collar. The spring can be locked into position until released, so as to allow for proper positioning of the device within the uterus. Unlocking the spring can then apply compression force or pressure on the exo cervix or external os with the cervical collar, thus pulling on the device proximally to seat the distal anchor as shown in FIG. 4H.

Once the device has been properly positioned, a heated vapor can be delivered from the distal tip 406 of ablation device 400 through vapor ports 407 into the uterus to ablate the uterine tissue. The vapor condenses on tissue and comes into direct contact with the tissue within the uterus. In some embodiments, the shaft of the uterine ablation device can include a thermocouple or other temperature sensor positioned proximally of the positioning balloon or sealing balloon to sense and indicate a vapor leak from the uterus into the cervical canal. In one embodiment, the ablation incorporates a pressure sensor in the uterine cavity. Upon completion of the ablation therapy or when a predetermined pressure has been achieved, the vapor can be removed from the uterus through the distal tip of the device. In one embodiment, the distal balloon 408 can be deflated immediately prior to, or during vapor delivery, so as to allow vapor to permeate and ablate the tissue that was formerly blocked by the distal balloon. This step is permissible and safe for the patient since sealing balloon 410 and positioning balloon 412 still provide dual redundancy for preventing vapor to escape back into the sensitive portions of the anatomy, such as the cervix and vagina.

In another method, the uterine ablation device can be positioned and used for treatment with only the distal anchor and central sealing balloon. In this embodiment, the uterine ablation device can be arranged in a delivery configuration and inserted through the vagina, cervical canal, and cervix of a patient to gain access to the uterus. Once the distal tip of the ablation device is disposed within the uterus, the distal anchor can be inflated or expanded. Upon inflating or expanding the distal balloon, the uterine ablation device can be pulled proximally (e.g., by a physician) to engage the interior portion of the cervix, the cervical ostium or internal os. When the ablation device is positioned against the internal os, the central sealing balloon can be inflated to seal the cervical canal from the uterus. Next, a heated vapor can be delivered from the ablation device through the vapor delivery ports to the uterus to ablate the uterine tissue. Upon completion of the ablation therapy or when a predetermined pressure has been achieved, the vapor can be removed from the uterus through the vapor return ports.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of delivering vapor to a uterus of a patient, comprising:
    inserting a portion of a uterine ablation device into the uterus of the patient;
    inflating a distal balloon of the uterine ablation device in the uterus;
    inflating a proximal balloon of the uterine ablation device against a cervical canal of the patient, against an external os of the patient, and into a vagina of the patient to pull the uterine ablation device proximally and place the distal balloon against an internal os of the patient;
    inflating a central balloon within the cervical canal; and
    delivering a heated vapor to the uterus to ablate uterine tissue.

2. The method of claim 1 wherein the inserting step further comprises inserting the uterine ablation device into the uterus of the patient so as to position a distal tip of the device distally to the internal os of the patient.

3. The method of claim 1 wherein the inflating the distal balloon step further comprises inflating the distal balloon distally to the internal os of the patient.

4. The method of claim 1 wherein the distal balloon has a donut shape.

5. The method of claim 1 wherein the inflating the central balloon step further comprises inflating the central balloon against a cervical canal and the internal os of the patient.

6. The method of claim 1 wherein the inflating the proximal balloon step is performed after the inflating the distal balloon step.

7. The method of claim 1 wherein the inflating the central balloon step is performed after the inflating the proximal balloon step.

8. The method of claim 1 further comprising; prior to the delivering step, collapsing the distal balloon of the uterine ablation device.

9. The method of claim 1, wherein the central balloon does not extend into the uterus or into the vagina of the patient when inflated.

* * * * *